United States Patent [19]

Forster et al.

[11] 3,989,751

[45] Nov. 2, 1976

[54] PROCESS FOR THE PREPARATION OF CARBOXYLIC ANHYDRIDES FROM OLEFINIC HYDROCARBONS

[75] Inventors: Denis Forster, University City; Arnold Hershman, Creve Coeur, both of Mo.

[73] Assignee: Monsanto Company, St. Louis, Mo.

[22] Filed: Dec. 12, 1974

[21] Appl. No.: 531,946

[52] U.S. Cl. ............................ 260/546; 260/514 M; 260/523 R; 260/533 A
[51] Int. Cl.² .......................................... C07C 51/54
[58] Field of Search ........... 260/546, 514 M, 523 R, 260/533 A

[56] References Cited
UNITED STATES PATENTS

| | | | |
|---|---|---|---|
| 2,473,993 | 6/1949 | Gresham et al. | 260/546 |
| 2,497,304 | 2/1950 | Gresham et al. | 260/546 |
| 2,549,453 | 4/1951 | Gresham et al. | 260/546 |
| 2,593,440 | 4/1952 | Hagemeyer | 260/546 |
| 2,658,075 | 11/1953 | Reppe et al. | 260/546 |
| 2,739,169 | 3/1956 | Hagemeyer | 260/546 |
| 2,768,968 | 10/1956 | Reppe et al. | 260/546 |
| 3,944,604 | 3/1976 | Hershman et al. | 260/533 A |

Primary Examiner—Norman Morgenstern

[57] ABSTRACT

The present invention relates to an improved process for the preparation of organic carboxylic acid anhydrides, specifically by the reaction of ethylenically unsaturated compounds having 2 to 30 carbon atoms with carbon monoxide and carboxylic acids or substances which yield carboxylic acids under reaction conditions at a temperature of 50° C to 300° C and a partial pressure of carbon monoxide of from 1 to 200 atm. in the presence of a catalyst composition essentially comprised of 1. a cobalt or nickel compound, and
2. an iodide component subject to the conditions that the atomic ratio of iodide to cobalt or nickel is from 1:1 to 300:1,
3. a catalyst preserver or regenerator component selected from the group consisting of hydrogen or a compound capable of giving rise to hydrogen under the reaction conditions. The process is particularly suited to the production of propionic anhydride.

9 Claims, No Drawings

PROCESS FOR THE PREPARATION OF CARBOXYLIC ANHYDRIDES FROM OLEFINIC HYDROCARBONS

This invention relates to an improved process for the production of carboxylic acid anhydrides. More particularly it relates to a process for the transformation of ethylenically unsaturated compounds having 2 to 30 carbon atoms and containing the structural unit.

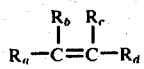

in aliphatic, acyclic or cycloaliphatic form where $R_a$, $R_b$, $R_c$ and $R_d$ are moieties having from 0 to 20 carbon atoms and are selected from the group consisting of hydrogen, halogen, alkyl, alkene, aryl, cycloaryl and cycloalkine moieties, which process comprises contacting the said compound with carbon monoxide and carboxylic acids. More particularly the process comprises the improvement of producing carboxylic acid anhydrides in the presence of catalyst compositions essentially comprising cobalt or nickel compounds or complexes, an iodide component, and a catalyst preserving or regenerating component consisting essentially of hydrogen or a compound capable of giving rise to hydrogen under the reaction conditions to yield carboxylic acid anhydrides selectively and efficiently at mild pressures.

Processes for the preparation of carboxylic acid anhydrides from olefins, and other ethylenically unsaturated compounds, carbon monoxide, and carboxylic acids are well known in the art. The prior art as exemplified in the article by R. E. Brookes, W. G. Graham, J. V. E. Hardy and J. M. Lupton [*Industrial and Engineering Chemistry* 49, 2004 (1957)] teaches the use of catalysts derived from carbonyls of nickel and cobalt for the synthesis of propionic anhydride from ethylene, carbon monoxide and propionic acid at very high pressures at high temperatures. Typical reaction conditions described by Brookes, et al, are temperatures of 270°–290° C and pressures of 300–600 atmospheres. Operating a process with such severe conditions requires specialized and expensive equipment making such a scheme commercially unattractive. Recently, noble metal catalysts have been found which are capable of synthesizing carboxylic acid anhydrides under much milder reaction conditions. Thus Fenton in U.S. Pat. No. 3,641,071 and U.S. Pat. No. 3,641,074 has described palladium catalysts which are capable of synthesizing carboxylic acid anhydrides from olefins, carbon monoxide and carboxylic acids under reaction conditions of 150°–200° C and 10–30 atmospheres. While these noble metal catalysts indeed offer great economic advantages because of the less severe reaction conditions required, they have some intrinsic disadvantages. Thus catalyst activity must be maintained for very long periods of time in order to justify using these very expensive materials. Extreme care must be taken in handling of reaction solutions to avoid losses of the noble metals.

STATEMENT OF THE INVENTION

It is therefore an object of the present invention to overcome the above disadvantages and, thus, provide an improved and commercially feasible carbonylation process for the production of carboxylic acid anhydrides from ethylenically unsaturated compounds in liquid phase and vapor phase processes. The process of this invention can be conducted in a batch or continuous operation.

In accordance with the present invention carboxylic acid anhydrides are obtained by reaction of ethylenically unsaturated compounds in the liquid phase or vapor phase with carbon monoxide and carboxylic acids under the reaction conditions of about 50° C to 300° C, preferably 125° C to 225° C, and at partial pressures of carbon monoxide from 1 atmospheric to 200 atmospheres preferably 2 atmospheres to 75 atmospheres, although higher pressure may be employed, in the presence of an improved catalyst system, essentially comprising a cobalt or nickel component, an iodide component, and a catalyst preserving or regenerating component consisting of hydrogen or a compound capable of giving rise to hydrogen under the reaction conditions.

Description of the Preferred Embodiments

The following equation illustrates the reaction which takes place when carboxylic acid anhydrides are produced from ethylenically unsaturated compounds having 2 to 30 carbon atoms, carbon monoxide, and carboxylic acids of the formula RCOOH, where R represents alkyl, cycloalkyl, aryl or aralkyl groups:

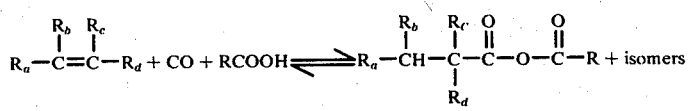

The ethylenically unsaturated reactant is an aliphatic, acyclic or cycloaliphatic form and $R_a$, $R_b$, $R_c$, and $R_d$ are moieties having from 0 to 20 carbon atoms and are selected from the group consisting of hydrogen, halogen, alkyl, alkene, aryl, cycloalkyl, and cycloalkene moieties.

Under certain reaction conditions, depending upon feedstocks and other parameters the isometric mixed anhydride may also be produced.

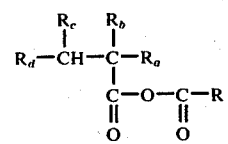

Simply anhydrides are formed to some extent by disproportionation of mixed anhydride products. For example, ethylene reacts with carbon monoxide and acetic acid to form the mixed acetic propionic anhydride $C_2H_5COOCOCH_3$, which then may disproportionate into propionic anhydride and acetic anhydride.

In a preferred embodiment ethylene reacts with carbon monoxide and propionic acid to form propionic anhydride in substantially the following manner:

In another embodiment of this invention the carboxylic acid which reacts with the olefin and carbon monoxide may be produced, at least in part, in situ, from substances which yield carboxylic acids under reaction conditions. Thus, the invention contemplates the synthesis of carboxylic acid anhydrides by introducing into a reaction vessel carbon monoxide, water, and ethylenically unsaturated compounds, in such quantities that the ethylenically unsaturated compounds and carbon monoxide are present in molar excess of the amount needed for conversion of all of the water to carboxylic acid at temperatures of 50° C to 300° C and a partial pressure of carbon monoxide of from 1 to 200 atmospheres in the presence of a catalyst system essentially comprising critical proportions of a cobalt or nickel component, a halide component, and a catalyst preserving or regenerating component consisting of hydrogen or a compound capable of giving rise to hydrogen under the reaction conditions.

When the carboxylic acid reactant is produced in situ the overall reaction may be written as follows:

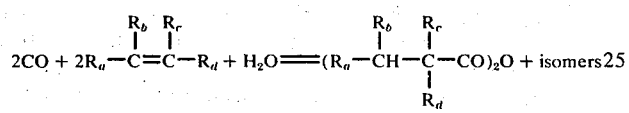

By control of the molar ratio of water to carbon monoxide, ethylenically unsaturated compounds and carboxylic acid (if desired) introduced into the reaction vessel, co-production of carboxylic acids and carboxylic acid anhydrides may be achieved. The criteria whether solely anhydride is produced or whether acid and anhydride are co-produced depends on $R_w$ which is the ratio of moles of water fed to the reactor per mole of carbon monoxide or olefin consumed (since carbon monoxide and the ethylenically unsaturated compounds are reacted in a 1 to 1 mole ratio, $R_w$ may be computed based on either of these reacting components). For values of $R_w \geq 1.0$ (equal to or greater than 1), no anhydride is formed; the products from the reactor are carboxylic acids. At values of $R_w >$ (greater than) 0.5 but $< 1.0$ (less than 1.0) carboxylic acid anhydrides and carboxylic acids are co-produced. Carboxylic acid anhydrides are the sole products when $R_w$ is 0.5. For values of $R_w < 0.5$ (less than 0.5), carboxylic acid must also be reacted from the feed to satisfy the relationship for anhydride synthesis through the equation.

Moles of carboxylic acid consumed
from the feed per mole of carbon     $= 1-(2 \times R_w)$
monoxide consumed.                   [for $R_w < 0.5$]

For example, feeding 0.75 moles of water to the reactor for every 1 mole of ethylene or carbon monoxide consumed ($R_w = 0.75$) co-produces 0.5 moles of propionic acid along with 0.25 moles of propionic anhydride. However, feeding 0.5 moles of water to the reactor for every mole of ethylene or carbon monoxide consumed ($R_w = 0.50$) yields substantially all propionic anhydride, and feeding 0.4 mols of water ($R_w = 0.4$) requires the consumption of 0.2 mole of propionic acid from the feed to synthesize 1 mole of propionic anhydride.

The reaction may also be conducted in essentially two stages by contacting the ethylenically unsaturated compound with carbon monoxide and water to produce carboxylic acid in the first stage and then contacting the resulting carboxylic acid product with more ethylenically unsaturated compound and carbon monoxide to produce the required carboxylic acid anhydride. Operating in the above manner with two reaction zones or in an elongated, heated conduit with intermediate addition of reactants appears to be beneficial to the catalyst system which does not deactivate as readily.

In all the above cases, it has also been discovered that critical control of the ratio of halide to metal of the carbonylation catalyst system is necessary as discussed herein, in addition to the critical control of feed ratios to obtain the desired anhydride in good yield.

Suitable ethylenically unsaturated feedstocks in the processes of this invention include ethylene, propylene, butene-1; butene-2; isopentene, hexenes, octenes, dodecenes; hexadecenes; 2-methylpentene; styrene; methylstyrene; vinylcyclohexene; 3,3-dimethyl-1-butene; 2-phenylbutene; 2-cyclohexylbutene; and mixtures thereof.

In addition to the simple olefinic hydrocarbons, other feedstocks may also be used, such as nitrogen substituted compounds, e.g. acrylonitrile; carboxyl substituted compounds, e.g. vinyl acetic acid; halogen substituted compounds, e.g. vinyl chloride; and hydroxy substituted compounds, e.g. allyl alcohol.

However, the preferred feedstocks are mono-olefinic hydrocarbons, including alpha- and internal olefins, such as ethylene, propylene, butene-1, butene-2, isobutylene, hexene-1, hexene-2, dodecene-1, dodecene-6, 3,3-dimethylbutene-1, and the like, most preferably ethylene.

Suitable carboxylic acid feedstocks in the process of this invention include acetic acid, propionic acid, heptanoic acids, tridecanoic acids, phenylacetic acid, toluic acid, 2-methyl valeric acid, and the like.

However, the preferred carboxylic acid feedstocks are low molecular weight saturated aliphatic carboxylic acids such as acetic acid and propionic acid.

Numerous organic carboxylic acid anhydrides are prepared by the process of this invention, such, for example, as the following: carbon monoxide reacting with propionic acid and ethylene gives propionic anhydride; carbon monoxide reacting with propylene and butyric acids gives butyric anhydrides; carbon monoxide reacting with isobutylene and 2-methylbutyric acid gives 2-methylbutyric anhydride; carbon monoxide reacting with dodecenes and tridecanoic acids gives tridecanoic anhydride, and the like.

The most preferred embodiments of the processes of this invention are the preparation of propionic anhydride from ethylene, and carbon monoxide, and propionic acid or water; and the preparation of the mixed acetic-propionic anhydride which disproportionates to acetic anhydride and propionic anhydride from ethylene, carbon monoxide, and acetic acid.

For purposes of the present invention, the catalyst system essentially includes a cobalt or nickel compound, an iodide component and a catalyst preserving or regenerating component consisting of hydrogen or a compound capable of giving rise to hydrogen under the reaction conditions.

Generally, the metal component of the catalyst system of the present invention is believed to be present in the form of a coordination compound of cobalt or nickel with a halogen component providing at least one of the ligands of such coordination compound. In this invention, these coordination compounds also generally include carbon monoxide ligands. Other moieties may be present if desired. Generally, it is preferred that the catalyst system contain as a promoting component, an excess of halogen over that present as ligands in the coordination compound. The terms "coordination compound" and coordination complex" used throughout this specification means a compound or complex formed by combination of one or more electronically poor molecules or atoms capable of independent existence with one or more electronically rich molecules or atoms, each of which may also be capable of independent existence.

The essential metal and halogen components of the catalyst system of the present invention may be provided by introducing into the reaction zone a coordination compound of cobalt or nickel containing halogen ligands or may be provided by introducing into the reaction zone separately a metal compound and a halogen compound. Among the materials which may be charged to the reaction zone to provide the metal component of the catalyst system of the present invention are cobalt or nickel metal, cobalt or nickel salts and oxides, organo-cobalt or -nickel compounds, compounds of cobalt and nickel, and the like. Specific examples of materials capable of providing the metal constituent of the catalyst system of the present invention may be taken from the following non-limiting partial list of suitable materials. Chemical and/or physical treatment of the metal precursor may be required, in order to render the cobalt or nickel moiety in the proper valence state and ligand environment. A partial list of suitable metal compounds follows:

| Co or Ni metal | $Ni[(C_6H_5)_3P]_2Br_2$ |
|---|---|
| | $Co(pyridine)_2I_2$ |
| $CoI_2$ or $NiI_2$ | $Ni(pyridine)_4Cl_2$ |
| $CoCl_2$ or $NiCl_2$ | $[(C_4H_9)_4N][Ni(CO)_3I]$ |
| $Co_2(CO)_8$ or $Ni(CO)_4$ | Co (acetylacetonate)$_2$ |
| $Co[C_6H_5)_3P]_2I_2$ | $Ni(cyclooctadiene)_2$ |
| $HCo(CO)_4$ | |
| $Co(CH_3CO_2)_2$ | |
| $Ni(CH_3CO_2)_2$ | |
| $CO(NO_3)_2 \cdot 6H_2O$ | |
| $Ni(NO_3)_2 \cdot 6H_2O$ | |

With those materials listed above as capable of providing the metal component which do not contain an iodine component it will be necessary to introduce into the reaction zone such as iodine component. For example if the cobalt component is cobalt acetate, it will be necessary to also introduce an iodide component such as ethyl iodide, hydrogen iodide, or the like.

As noted above, while the halogen component of the catalyst system may be in combined form with the cobalt or nickel as for instance, one or more ligands in a coordination compound, it is generally preferred to have an excess of an iodine-containing compound in the catalyst system as a promoting component. This promoting component of the catalyst system consists of an iodine-containing compound such as hydrogen iodide, alkyl or aryl iodide, metal iodide, ammonium iodide, phosphonium iodide, arsonium iodide, and the like. The halogen of the promoting component may be the same or different from that already present as ligands in the coordination sphere of the metal. Accordingly, suitable iodine providing or promoting components may be selected from the following list of compounds.

| RI | where | R = any alkyl - or aryl-group e.g., $C_2H_5I$ |
|---|---|---|
| $I_2$ | | |
| HI | | |
| $RCl \atop \| \atop O$ | where | $R = $ any alkyl- or aryl-group e.g., $CH_3Cl \atop \| \atop O$, etc. |
| $R_4MI$, | | |
| $R_4MI_3$, | where | R = hydrogen or any alkyl or aryl |
| $R_3MI_2$ | and | M = N, P, As, or Sb |

It has been discovered that critical ratios of iodide to active metal catalyst, expressed as atoms of halide to atoms of metal atom exist. Within the range of these critical ratios, very reactive and selective carbonylation to carboxylic acid anhydrides occurs at milder temperatures and pressures than were heretofore possible.

The optimum critical ratios of iodine atoms to atoms of cobalt or nickel are in the range of 1:1 to 300:1 and preferably 4:1 to 100:1.

Outside the range of critical ratios of iodide to metal atoms, particularly at the higher iodide levels, the reaction efficiency and yield is drastically reduced. For example, at the higher halide levels, significantly higher partial pressure of carbon monoxide is required for the reaction to proceed at an appreciable rate. Also, at the higher iodide levels, i.e., higher ratio of iodide to metal, the specificity to carboxylic acid anhydride product is significantly reduced and numerous oxygenated by-products such as ketones, lactones, aldehydes, etc. are formed.

The use of such low ratios of iodide to metal in contradistinction to the prior art, also simplifies the processing required, decreases handling of the expensive halide component and allows cheaper materials of construction, thus providing an improved, more economical, and commercially feasible process for the production of carboxylic acid anhydrides.

The exact nature of the optimum critical ratio of iodine to metal atom of the catalytic system has not been completely elucidated and may vary as a function of other reaction parameters including solvent composition, absolute concentration of catalyst components, e.g., metal and iodide constituents.

Generally, it is preferred that the process of the present invention be carried out in an acidic reaction medium. For purposes of the present invention, an acidic reaction medium is defined as one in which an alkyl iodide is present or will be formed. For example, when the feed is ethylene, the alkyl iodide will be the ethyl iodide. Such alkyl iodide may be added to the reaction medium as such or may be formed in situ within the reaction medium from the ethylene feed and the iodide present in the catalyst system. The reaction medium is considered acidic when under reaction conditions as herein set forth, at least 0.1% by weight of the total iodine in the system is present as the alkyl iodide. It is preferred, however, that at least 1.0% by weight of the total iodine in the system is present as the alkyl iodide.

The preparation of the active catalyst complex which includes both metal and iodide components may be accomplished by a variety of methods. In general, in the process of this invention, it is convenient to perform the active carbonylation catalyst system which contains both metal and iodide components. For example, to prepare the catalyst system, the metal component of the catalyst system, e.g. finely divided cobalt or nickel metal (powder); a simple cobalt or nickel salt or compound as a precursor is dissolved in a suitable medium, and carbon monoxide is bubbled through the above solution, preferably while maintaining gentle heating and stirring of the solution. Then a solution of the desired iodide promoter source is added to form an active catalytic solution containing the necessary metal and iodide promoter components.

The catalyst preserving or regenerating component of the catalyst system consists of hydrogen or a compound which generates hydrogen under the reaction conditions. Examples of compounds which generate hydrogen under the reaction conditions are sodium borohydride and hydrazine. This catalyst preserving or regenerating component may be employed in several ways. The component may be continually fed to the reactor during the course of the reaction. Alternatively, the catalyst returning to the reactor following separation of the product by, say, distillation, may be treated with the regenerating component of the catalyst system before being contacted with the reactants, namely carbon monoxide and the ethylenically unsaturated hydrocarbon. The catalyst preserving or regenerating component of the catalyst system can be employed at any reasonable level in the system but best results are obtained if the molar ratio of preserver or regenerator component to metal containing component is 5:1 to 10,000:1.

The ability of the preserver or regenerator component, namely hydrogen or a hydrogen-generating component to maintain or regenerate the activity of the cobalt or nickel catalysts is unique for the iodide promoted systems. Catalyst systems employing other halides, e.g., bromide or chloride, as promoters have also been investigated but such systems have shown a tendency to rapidly deactivate and these systems could not be regenerated by use of hydrogen. Further, their activity could not be maintained by continually supplying hydrogen to the reaction.

The preservative and regenerative ability of hydrogen or hydrogen-generating substances as described herein has been found to be unique to cobalt and nickel systems and appears to be much less effective in preserving or regenerating the catalyst systems described in the prior art containing other metals which also are known to suffer from rapid deactivation under the conditions required for carboxylic acid anhydride synthesis.

The reason for the catalyst deactivation observed in systems for the synthesis of carboxylic acid anhydrides is unknown at this time, but in view of the well-known strongly reducing character of two of the prinicipal reactants, namely carbon monoxide and ethylenically unsaturated compounds, it might logically be supposed that the deactivation process involves reduction of the active form of the metal catalysts; perhaps, to an inactive lower valence state or to the metal itself. In view of this, it was quite unexpected to find that the activity of the iodide promoted cobalt and nickel systems could be preserved by introduction of a component consisting of a strong reducing agent, namely hydrogen or a hydrogen producing substance. Further, it has been discovered that the full activity of systems which have suffered either partial or total deactivation can be regenerated by use of hydrogen or a compound capable of giving rise to hydrogen under the reaction conditions.

The catalyst system of the present invention is unique in comparison to earlier work in that it does not require the use of anhydrous or highly concentrated mineral acid solutions. Furthermore the present catalyst system permits the use of halogen sources such as alkyl halides, e.g., ethyl iodide in place of the highly corrosive mineral acids such as concentrated HI. These factors serve greatly to reduce the corrosivity of the reaction system.

The present invention is based upon the production of carboxylic acid anhydrides by the reaction of ethylenically unsaturated compounds, carbon monoxide, and carboxylic acids or substances which yield carboxylic acids under reaction conditions.

In accordance with the present invention, the carbonylation reaction may be carried out by intimately contacting olefins with gaseous carbon monoxide and carboxylic acids in a liquid phase containing the catalyst system prepared from cobalt or nickel precursors; in the presence of an iodide component and a catalyst preservative or regenerator component consisting of hydrogen, under conditions of temperature and pressure suitable as described herein to form the anhydride product. The temperature accordingly is in the range of 50° C to 300° C. Partial pressures of carbon monoxide of the order of 1 atmosphere to 200 atmospheres may be employed; however, 2 atmospheres to 75 atmospheres carbon monoxide partial pressure is generally preferred. These modest pressure requirements contrast markedly with those of prior art catalyst system employing first row transition metals. Higher pressures may be used if desired via reaction of olefins with carbon monoxide and carboxylic acids in the vapor phase over the cobalt or nickel containing catalyst systems described above, dispersed upon solid, inert supports. Such a catalyst may be operated as a conventional fixed bed catalytic reactor. For example, ethylene, ethyl iodide, carbon monoxide and propionic acid and a small amount of hydrogen may be passed over a catalyst system consisting, for example, of $CoI_2$ dispersed on a solid support material such as alundum, activated carbon, clays, alumina, silica-alumina, and ceramics, etc., in a fixed bed reactor maintained at elevated temperature and pressure, as described above, to produce propionic anhydride in high yields. However, use of a liquid reaction medium is preferred in the process of this invention using dissolved or dispersed active catalytic and promoter components.

A typical carbonylation reaction selective to carboxylic acid anhydrides requires at least one mole of carbon monoxide, one mole of carboxylic acid, and one mole of ethylenically unsaturated component per mole of anhydride product. Excess of carbon monoxide, carboxylic acid, olefin, as discussed above over the aforesaid stoichiometric amounts, however, may be present. Carbon monoxide streams containing inert impurities such as carbon dioxide, methane, nitrogen, noble gases, and paraffinic hydrocarbons having from 1 to 4 carbon atoms, may be employed, if desired, for example, from an available plant gas stream, with no ill effect; however, in such cases total reactor pressure will have to be increased to maintain a desired carbon monoxide partial pressure. The concentration of carbon monoxide in the feed gas mixture is from 1 vol. % to 99.9 vol %, a preferred range being from 10 vol % to 99.9 vol %.

The reaction rate is dependent upon catalyst concentration and temperature. Concentrations of the cobalt or nickel compound or the first component of the catalyst system in the liquid phase, between $10^{-6}$ moles/liter and 1 moles/liter, are normally employed, with the preferred range being $10^{-2}$ moles/liter to 0.5 moles/liter. Higher concentrations may, however, be used if desired. Higher temperatures also favor higher reaction rates.

The concentration of the second component or iodide portion of the catalyst system may vary over the broad concentration range of $10^{-6}$ moles/liter to 18 moles/liter, based on iodide atoms. In the process of this invention, however, the preferred critical range of ratios of iodide atoms to metal atoms is maintained as discussed herein to achieve the superior results.

The present invention may be practiced with or without the employment of an added solvent. The use of a solvent, which preferably boils at a higher temperature than the desired carboxylic acid anhydride product, gives certain processing advantages e.g. more complete product separation upon distillation.

The halide promoted cobalt and nickel catalysts of the present invention are characterized by a high degree of specificity for the carboxylation reaction to anhydrides.

For a better understanding of the processes of the present invention specific embodiments of the process are presented below. These examples and illustrations are not to be construed in any way as limiting the scope of the invention.

EXAMPLE 1

A batch reactor provided with a stirrer is charged with the following ingredients: 3.2 grams ($1.02 \times 10^{-2}$ moles) of a cobalt compound having the formula $CoI_2$ which provides both the catalyst precursor and the iodide promoter; and 85 ml. of propionic acid as reactant; the olefin feed, ethylene is charged to the reactor as a 1:1 molar mixture with carbon monoxide.

The reactor is pressurized with the gas blend to a total pressure of 67 atmospheres (partial pressure of carbon monoxide about 23 atmospheres) at 195° C. The reaction is carried out at a constant pressure by feeding the gas blend upon demand, from a high pressure reservoir.

Over a period of 50 minutes no reaction occurs as evidenced by a lack of gas uptake. Hydrogen (2 atmospheres partial pressure) is then introduced to the reactor. A reaction begins as indicated by gas uptake. The reaction is allowed to proceed for a further four hours.

A liquid sample is removed from the reactor and the product analyzed by a gas chromatographic technique yields a solution containing:
 6.7% propionic anhydride
 70.2% propionic acid If cobalt carbonyl or cobalt acetate is used in place of cobalt iodide in the above experiment, no propionic anhydride is formed in the reaction. This illustrates that the iodide component is also essential to the invention.

EXAMPLE 2

This example demonstrates that the concept of use of added hydrogen as a preserving or regenerating component for synthesis of carboxylic acid anhydrides from olefins, carbon monoxide and carboxylic acids, applies also to the nickel/iodide catalyst system.

A batch reactor is charged with the following ingredients: 3.2 grams of $NiI_2$ (0.01 moles) as the catalyst precursor, and 85 ml of propionic acid as a reactant: the olefin feed, ethylene is charged to the reactor as a 1:1 molar mixture with carbon monoxide.

The reactor is pressurized with the bas blend to a total pressure of 67 atmospheres (partial pressure of carbon monoxide about 23 atmospheres) at 195° C. The reaction is carried out at constant pressure by feeding the gas blend upon demand, from a high pressure reservoir. A very slow gas uptake is noted (0.18 g-moles/1-hr.) After 2 hours, hydrogen (3 atmospheres partial pressure) is added, whereupon a greater than six-fold increase in reaction rate is observed. After a further 4 hours a sample is removed from the reactor and analyzed by a gas chromatographic technique. The sample is found to contain:
 27.5% propionic anhydride
 65.8% propionic acid.

EXAMPLE 3

A batch reactor provided with a stirrer is charged with the following ingredients: 2.49 grams ($1.0 \times 10^{-2}$ moles) of a cobalt compound of formula $Co(CH_3CO_2)_2 \cdot 4H_2O$ which provides the catalyst precursor; 15.6 grams of ethyl iodide (0.10 moles) as the promoter component; and 85 ml of propionic acid as reactant; the olefin feed, ethylene is charged to the reactor as a 1:1 molar mixture with carbon monoxide.

The reactor is pressurized with the gas blend to a total pressure of 67 atmospheres (partial pressure of carbon monoxide, about 23 atmospheres) at 195° C. The reaction is carried out at a constant pressure by feeding the gas blend upon demand, from a high pressure reservoir.

Over a period of 1 hour no reaction occurs as indicated by a lack of gas uptake. Hydrogen (3 atmospheres partial pressure) is then introduced to the reactor. A reaction begins immediately as shown by gas uptake. The reaction is allowed to proceed for a further 3 hours.

A liquid sample is removed from the reactor and the product analyzed by a gas chromatographic technique yields a solution containing
 8.3% propionic anhydride
 73.5% propionic acid.

What is claimed is:

1. An improved process for the production of carboxylic acid anhydrides by the reaction of ethylenically unsaturated feedstock compounds having from 2 to 30 carbon atoms, which comprises contacting the said compound with carbon monoxide, and at least one reactant selected from the group consisting of carboxylic acids having from 2 to 30 carbon atoms and water, at a temperature from 50° C to 300° C and a partial pressure of carbon monoxide of 1 atmosphere to 200 atmospheres, the improvement comprising the production of carboxylic acid anhydrides in the presence of a catalyst system comprised of:
 1. a cobalt or nickel compound and
 2. an iodide component subject to the conditions that the atomic ratio of iodide to cobalt or nickel is from 1:1 to 300:1, and
 3. hydrogen as a catalyst preserver or regenerator component in the molar ratio of 5:1 to 10,000:1 relative to the said cobalt or nickel.

2. Process as in claim 1 in which the reactants of the group of carboxylic acids and water are carboxylic acids having from 2 to 30 carbon atoms.

3. Process as in claim 1 in the presence of both carboxylic acids having from 2 to 30 carbon atoms and water as reactant wherein the ratio of moles of water fed to the reactor per mole of carbon monoxide consumed is less than 0.5.

4. Process as in claim 1 in which the reactant of the group of carboxylic acids and water, is water, wherein the ratio of moles of water fed to the reactor per mole of carbon monoxide consumed is at least 0.5 but less than 1.0.

5. Process as in claim 1 in which the said cobalt compound is cobalt iodide.

6. Process as in claim 1 in which the said nickel compound is nickel iodide.

7. Process as in claim 1 in which the said iodide component is an alkyl iodide having from 1 to 20 carbon atoms.

8. Process as in claim 1 in which the said ethylenically unsaturated compound is ethylene and the reactant of the group of carboxylic acids and water is propionic acid and the product is comprised of propionic anhydride.

9. Process as in claim 1 in which the partial pressure of carbon monoxide is from 2 atmospheres to 75 atmospheres.

* * * * *